United States Patent
Chen et al.

(10) Patent No.: US 10,106,513 B2
(45) Date of Patent: Oct. 23, 2018

(54) METHOD FOR PREPARING 2-MERCAPTOBENZOTHIAZOLE

(71) Applicant: Sennics Co., Ltd., Shanghai (CN)

(72) Inventors: Xinmin Chen, Shanghai (CN); Libao Wu, Shanghai (CN); Song Shi, Shanghai (CN); Shang Gao, Shanghai (CN)

(73) Assignee: Sennics Co., Ltd., Shanghai (CN)

( * ) Notice: Subject to any disclaimer, the term of this patent is extended or adjusted under 35 U.S.C. 154(b) by 0 days.

(21) Appl. No.: 15/948,321

(22) Filed: Apr. 9, 2018

(65) Prior Publication Data

US 2018/0222875 A1    Aug. 9, 2018

Related U.S. Application Data

(63) Continuation of application No. PCT/CN2015/093613, filed on Nov. 2, 2015.

(30) Foreign Application Priority Data

Oct. 9, 2015    (CN) .......................... 2015 1 0649388

(51) Int. Cl.
   *C07D 277/72*    (2006.01)
   *B01J 31/02*    (2006.01)
   *B01J 21/14*    (2006.01)
   *B01J 21/04*    (2006.01)

(52) U.S. Cl.
   CPC ............ *C07D 277/72* (2013.01); *B01J 21/04* (2013.01); *B01J 21/14* (2013.01); *B01J 31/0225* (2013.01); *B01J 31/0284* (2013.01)

(58) Field of Classification Search
   CPC .................................................. C07D 277/72
   USPC ......................................................... 548/176
   See application file for complete search history.

(56) References Cited

U.S. PATENT DOCUMENTS

| 5,367,082 | A | * | 11/1994 | Bergfeld | ............. | C07D 277/72 548/175 |
| 6,222,041 | B1 | * | 4/2001 | Reynolds | ............. | C07D 277/72 548/176 |

FOREIGN PATENT DOCUMENTS

| CN | 101508675 A | 8/2009 |
| CN | 102070562 A | 5/2011 |
| CN | 102304099 A | 1/2012 |

OTHER PUBLICATIONS

Zhu, Qiang et al., "Progress of Sulfonic Acid Functional Ionic Liquids in Organic Synthesis," Chemical Production and Technology, vol. 18, No. 2, pp. 38-44 (Dec. 31, 2011).

Liu, Ruijiang et al., "Optimization of Synthesis of 2-Mercapto Benzothiazole with Response Surface Methodology," Chemical Industry and Engineering Progress, vol. 28, No. 1, pp. 155-158 and 172 (Dec. 31, 2009).

* cited by examiner

*Primary Examiner* — Nyeemah A Grazier
(74) *Attorney, Agent, or Firm* — Mei & Mark LLP; Manni Li

(57) ABSTRACT

A method for preparing 2-mercaptobenzothiazole where the aniline method is adopted to perform reaction in the presence of a catalyst, and the catalyst includes sulfonic acid type imidazolium ionic liquid. The sulfonic acid type imidazolium ionic liquid is a type of acidic functionalized ionic liquid, and has the advantages of both a solid acid and a liquid acid. The sulfonic acid type imidazolium ionic liquid is adopted as an active ingredient of the catalyst, and may remarkably improve a conversion rate of the reaction raw materials and increase a yield of the 2-mercaptobenzothiazole. Meanwhile, due to the characteristics of high catalytic activity, no volatilization, low corrosion, high thermal stability and the like of the 2-mercaptobenzothiazole, the preparation method also has the comprehensive advantages of simple process, low cost, low tar yield, high environment friendliness and the like.

17 Claims, No Drawings

METHOD FOR PREPARING 2-MERCAPTOBENZOTHIAZOLE

CROSS-REFERENCE TO RELATED APPLICATIONS

The subject application is a continuation of PCT/CN2015/093613 filed on Nov. 2, 2015, which claims priority on Chinese Patent Application No. 201510649388.2 filed on Oct. 9, 2015 in China. Both PCT international application and Chinese priority application are incorporated herein by reference.

TECHNICAL FIELD

The present invention relates to the field of organic synthesis, and particularly, to a method for preparing 2-mercaptobenzothiazole.

BACKGROUND

2-Mercaptobenzothiazole, also known as Accelerator M or Accelerator MBT, and further called as "quick heating powder," is a general-purpose rubber vulcanization accelerator. It has the characteristics of fast vulcanization acceleration action, low vulcanization flatness, no early vulcanization during mixing and the like, and is widely applied to the rubber processing industry.

There are many synthesis methods for 2-mercaptobenzothiazole, and according to the raw materials, may be divided into an o-nitrochlorobenzene method, an aniline method, a mixed nitrobenzene and aniline method, a nitrobenzene method, a nitroso-benzene method, etc. The o-nitrochlorobenzene method, the aniline method, and the mixed nitrobenzene and aniline method are more frequently used. However, when the o-nitrochlorobenzene method is used for producing 2-mercaptobenzothiazole, the cost of the raw materials is high and the production process is complex, so that it is unsuitable for industrial application. The mixed nitrobenzene and aniline method is low in production cost and may reduce $H_2S$ produced by reaction by ⅓ of the aniline method, but it has the problems of difficulties in control of the reaction and high requirements on material of reactor, so currently, the method is less frequently used in China. Therefore, the aniline method for synthesizing 2-mercaptobenzothiazole is the method that has been generally adopted by each manufacturer for the agent.

The aniline method for producing 2-mercaptobenzothiazole has the characteristics of stable raw material sources, low difficulties in operation, and low requirements for the quality of the reactor. However, it still has the shortcomings of relatively low purity of the product, high amount of tar, relatively low yield, etc.

SUMMARY OF THE INVENTION

The present invention provides a method for preparing 2-mercaptobenzothiazole, so as to solve the problems of relatively low purity of the product, high tar production, and relatively low yield when 2-mercaptobenzothiazole is produced by the aniline method in prior art.

The method for preparing 2-mercaptobenzothiazole of the present invention comprises the following: the aniline method is adopted to perform the reaction in the presence of a catalyst to prepare 2-mercaptobenzothiazole, and the catalyst comprises sulfonic acid type imidazolium ionic liquid.

Furthermore, in the present invention, the sulfonic acid type imidazolium ionic liquid is [TSVM]$HSO_4$ and/or [MPS]$_2HSO_4$.

Furthermore, in the present invention, the catalyst further comprises a carrier for supporting the sulfonic acid type imidazolium ionic liquid.

Furthermore, in the present invention, the carrier is selected from one or more of a group formed by an activated alumina, cordierite honeycomb ceramics, mercaptoalkyl-functionalised silica gel, an ion exchange resin and an HZSM molecular sieve (Hydrogen type Zeolite Sieve of Molecular porosity molecular sieve).

Furthermore, in the present invention, a weight ratio of the sulfonic acid type imidazolium ionic liquid and the carrier is (0.1~20):100.

Furthermore, in the present invention, a reaction temperature of the reaction is 200~280° C., reaction pressure is 3.0~8.0 MPa, and reaction time is 2~12 hours.

Furthermore, in the present invention, the reaction temperature of the reaction is 240~250° C., the reaction pressure is 4.5~5.5 MPa, and the reaction time is 4~6 hours.

Furthermore, in the present invention, in the aniline method, aniline, carbon disulfide, and sulfur are taken as reaction raw materials, a molar ratio of the aniline, the carbon disulfide and the sulfur is 1:(1.0~1.3):(1.1~2), and a weight ratio of the aniline and the sulfonic acid type imidazolium ionic liquid is 100:(1~5).

Furthermore, in the present invention, the molar ratio of the aniline, the carbon disulfide, and the sulfur is 1:(1.0~1.1):(1.2~1.5), and the weight ratio of the aniline and the sulfonic acid type imidazolium ionic liquid is 100:(1~2).

Furthermore, in the present invention, the 2-mercaptobenzothiazole is prepared by adopting an intermittent or continuous production process.

In the preparation method of the present invention, the aniline method is adopted to prepare the 2-mercaptobenzothiazole with a catalytic action of the sulfonic acid type imidazolium ionic liquid. The sulfonic acid type imidazolium ionic liquid is a type of acidic functionalized ionic liquid, and has the advantages of both a solid acid and a liquid acid. In the present invention, the sulfonic acid type imidazolium ionic liquid is adopted as an active ingredient of the catalyst, and may remarkably improve a conversion rate of the reaction raw materials and increase a yield of the 2-mercaptobenzothiazole. Meanwhile, due to the characteristics of high catalytic activity, no volatilization, low corrosion, high thermal stability and the like of the 2-mercaptobenzothiazole, the preparation method of the present invention also has the comprehensive advantages of simple process, low cost, low tar yield, high environment friendliness and the like.

DETAILED DESCRIPTION OF THE INVENTION AND EMBODIMENTS

It is important to note that embodiments in the application and characteristics in the embodiments may be combined if they are not conflicting with each other. The present invention is described in details in connection with the following embodiments.

As described in the Background, when 2-mercaptobenzothiazole is produced by the aniline method, there exist the problems of relatively low purity of a product, high tar production, and relatively low yield. In order to solve the problems, the present invention provides a method for preparing 2-mercaptobenzothiazole. The aniline method is adopted to perform reaction in the presence of a catalyst to prepare the 2-mercaptobenzothiazole, and the catalyst includes sulfonic acid type imidazolium ionic liquid.

In the preparation method of the present invention, the aniline method is adopted to prepare the 2-mercaptobenzothiazole under a catalytic action of the sulfonic acid type imidazolium ionic liquid. The sulfonic acid type imidazolium ionic liquid is a type of acidic functionalized ionic liquid, and has the advantages of both a solid acid and a liquid acid. In the present invention, the sulfonic acid type imidazolium ionic liquid is adopted as an active ingredient of the catalyst, and may remarkably improve a conversion rate of the reaction raw materials and increase a yield and a purity of the 2-mercaptobenzothiazole. Meanwhile, due to the characteristics of high catalytic activity, no volatilization, low corrosion, high thermal stability and the like of the 2-mercaptobenzothiazole, the preparation method of the present invention also has the comprehensive advantages of simple process, low cost, low tar yield, high environment friendliness, etc.

In the preparation method of the present invention, as long as the sulfonic acid type imidazolium ionic liquid is adopted to catalyze the reaction between aniline, carbon disulfide, and sulfur as the active ingredient, a reaction process may be endowed with the advantages of high yield, low cost, environment friendliness, etc. In a preferred embodiment, the sulfonic acid type imidazolium ionic liquid is [TSVM]HSO$_4$ and/or [MPS]$_2$HSO$_4$.

The structure of the [TSVM]HSO$_4$ ionic liquid is as follows:

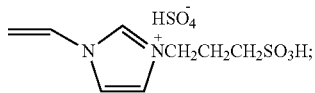

The structure of the [MPS]$_2$HSO$_4$ ionic liquid is as follows:

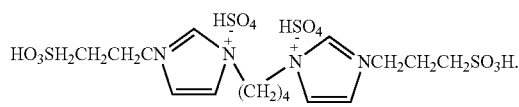

Both types of the sulfonic acid type imidazolium ionic liquid have relatively high catalytic activity, and are relatively low in cost and extensive in source, and using them as the active ingredient of the catalyst may further increase the yield of the 2-mercaptobenzothiazole, reduce emissions of waste gas, waste water and sold waste, and reduce production cost.

In the preparation method of the present invention, the sulfonic acid type imidazolium ionic liquid may be directly adopted to catalytically prepare the 2-mercaptobenzothiazole as a catalyst, that is, non-supported sulfonic acid type imidazolium ionic liquid may be directly added into a reaction system for catalytic reaction. In a preferred embodiment, a supported sulfonic acid type imidazolium ionic liquid is adopted as a catalyst, that is, the catalyst further includes a carrier for supporting the sulfonic acid type imidazolium ionic liquid. The supported sulfonic acid type imidazolium ionic liquid catalyst not only is applied to catalytic reaction in an ordinary intermittent reaction kettle or kettle type continuous reactor, but also may be mounted in a fixed tower to realize continuous production by continuous input and output of reaction raw materials, and has the advantages of relatively high yield, relatively low energy consumption, relatively low production cost, etc.

According to the present invention, those skilled in the art may select a concrete carrier of the supported sulfonic acid type imidazolium ionic liquid catalyst In a preferred embodiment, the carrier includes, but not limited to, one or more of an active alumina, a cordierite honeycomb ceramics, a mercaptoalkyl-functionalised silica gel, an ion exchange resin, and an HZSM molecular sieve. All of these carriers have the advantages of stable physical properties, large specific surface area, and relatively better bonding action with the sulfonic acid type imidazolium ionic liquid. In addition, these carriers are also relatively low in cost.

In the supported catalyst, those skilled in the art may select a proportional relationship between the catalytic active ingredient and the carrier. In a preferred embodiment, a weight ratio of the sulfonic acid type imidazolium ionic liquid and the carrier is (0.1~20):100; the relationship between the amount of the two used in the reaction is set within the above-mentioned range, so that the active ingredient of the catalyst may be dispersed on the carrier more uniformly, and relatively high catalytic activity is achieved. Meanwhile, cost may also be reduced, and difficulties in reaction operations may be reduced.

In a preferred embodiment, a reaction temperature of the reaction in the preparation process is 200~280° C., reaction pressure is 3.0~8.0 MPa, and reaction time is 2~12 hr. In the preparation method of the present invention, the sulfonic acid type imidazolium ionic liquid is adopted as the catalytic active ingredient, so that difficulties in operations for the 2-mercaptobenzothiazole may be reduced, and reaction conditions may be milder. The temperature, the pressure, and the time conditions are favorable for increasing a reaction rate, simultaneously reducing occurrence of side reaction, and endowing the reaction with a relatively high rate and yield. More preferably, the reaction temperature of the reaction is 240~250° C., the reaction pressure is 4.5~5.5 MPa, and the reaction time is 4~6 hr.

In the preparation method of the present invention, those skilled in the art may select a proportional relationship among the amount of each raw material used in the reaction. In a preferred embodiment, in the aniline method, aniline, carbon disulfide, and sulfur are taken as reaction raw materials, a molar ratio of the aniline, the carbon disulfide and the sulfur is 1:(1.0~1.3):(1.1~2), and a weight ratio of the aniline and the sulfonic acid type imidazolium ionic liquid is 100:(1~5). Setting the ratio of the amounts of each raw material within the range is favorable for further increasing the conversion rate of the reaction and simultaneously achieving a higher reaction speed and a higher target product yield. In addition, controlling the amount of the catalyst within the above-mentioned range is also favorable for reducing the cost and making the whole reaction more applicable to industrial large-scale application. More preferably, the molar ratio of the aniline, the carbon disulfide, and the sulfur is 1:(1.0~1.1):(1.2~1.5), and the weight ratio of the aniline and the sulfonic acid type imidazolium ionic liquid is 100:(1~2).

The preparation method of the present invention is applied to any production mode. In a preferred embodiment, the 2-mercaptobenzothiazole is prepared by adopting a batchwise or continuous production process. Batchwise refers to batchwise process using a batchwise catalytic kettle for the reaction, and continuous refers to a continuous process using a continuous tower for the reaction (for example, a fixed bed reaction or a trickle bed reaction).

The present invention is further described in details in connection with the following examples, and the examples do not serve to limit the scope of protection for the present invention.

Example 1

Ninety-three (93) grams of aniline, 76 grams of carbon disulfide, and 38.4 grams of sulfur (a molar ratio of the three is 1:1:1.2) are added to a pressure reactor, and 1.86 grams of non-supported sulfonic acid type imidazolium ionic liquid [TSVM]HSO$_4$ (a weight ratio between aniline and the [TSVM]HSO$_4$ is 100:2) is added into a system. The reaction temperature is controlled at 250° C., reaction pressure is controlled at 4.5 MPa, and after 6 hours of reaction, crude product melt is obtained.

The crude product melt is pressed into a crystallizer containing a toluene solvent, while hydrogen sulfide discharged therefrom is absorbed and treated with an alkali liquor, and after the melt is crystallized, washing, filtering and drying are performed to obtain a 2-mercapto benzothiazole product, where the product has a purity 98% or more and a yield of 90%.

Examples 2 to 7

The method for preparing 2-mercaptobenzothiazole is the same as Example 1, and the difference is in the reaction temperature, pressure, and time. The process conditions and resulted products of each example are shown in the following table.

|  | Reaction temperature (° C.) | Reaction pressure (MPa) | Reaction time (h) | Product purity (%) | Product yield (%) |
|---|---|---|---|---|---|
| Example 2 | 240 | 5.5 | 6 | 98 | 92 |
| Example 3 | 240 | 4.0 | 4 | 97.5 | 92 |
| Example 4 | 200 | 8.0 | 12 | 97 | 84 |
| Example 5 | 200 | 8.0 | 14 | 97.2 | 83 |
| Example 6 | 280 | 3.0 | 2 | 95.4 | 84 |
| Example 7 | 300 | 10.0 | 2 | 96.3 | 83 |

Examples 8 to 13

The method for preparing 2-mercaptobenzothiazole is the same as Example 1, and the difference is in the molar ratios of each raw material. The ratios of the raw material and resulted product of each example are shown in the following table:

|  | Molar ratio of aniline, carbon disulfide and sulfur | Weight ratio of aniline and [TSVM]HSO$_4$ | Product purity (%) | Product yield (%) |
|---|---|---|---|---|
| Example 8 | 1:1.1:1.5 | 100:2 | 98 | 90 |
| Example 9 | 1:1.1:1.5 | 100:1 | 98 | 89 |
| Example 10 | 1:1.1:1.1 | 100:3 | 97 | 91 |
| Example 11 | 1:1.1:2 | 100:4 | 97 | 92 |
| Example 12 | 1:1.3:2 | 100:5 | 98 | 90 |
| Example 13 | 1:1:1 | 100:10 | 98 | 92 |

Examples 14 to 19

The method for preparing 2-mercaptobenzothiazole is the same as Example 1, and the difference is in the types of the catalyst. The types of catalyst and resulted product of each example are shown in the following table:

|  | Catalyst | | | | Product purity (%) | Product yield (%) |
|---|---|---|---|---|---|---|
|  | Sulfonic acid type imidazolium ionic liquid | | Carrier | | | |
|  | Type | Weight (g) | Type | Weight (g) | | |
| Example 14 | [TSVM]HSO$_4$ | 1.86 | HZSM molar sieve | 9.3 | 97 | 90 |
| Example 15 | [TSVM]HSO$_4$ | 1.86 | HZSM molar sieve | 18.6 | 98 | 91 |
| Example 16 | [TSVM]HSO$_4$ | 0.37 | HZSM molar sieve | 370 | 94 | 87 |
| Example 17 | [MPS]$_2$HSO$_4$ | 1.86 | NONE |  | 96 | 91 |
| Example 18 | [MPS]$_2$HSO$_4$ | 1.86 | cordierite honeycomb ceramics | 6.2 | 98 | 92 |
| Example 19 | [TSVM]HSO$_4$/[MPS]$_2$HSO$_4$ (weight ratio: 1:1) | 1.86 | mercaptoalkyl-functionalised silica gel | 7.4 | 98 | 90 |

The above examples show that the sulfonic acid type imidazolium ionic liquid is adopted as the active ingredient of the catalyst, and may remarkably improve a conversion rate of the reaction raw materials and increase a yield of the 2-mercaptobenzothiazole. Meanwhile, the preparation method of the present invention also has the comprehensive advantages of simple process, low cost, low tar yield, high environment friendliness and the like.

The above preferred embodiments of the present invention do not intended to limit the scope of the present invention. For those skilled in the art, the present invention may have various modifications and variations. Any modifications, equivalent replacements, improvements, etc. made within the spirit and principle of the present invention shall fall within the scope of protection.

We claim:
1. A method for preparing 2-mercaptobenzothiazole, comprising
    reacting aniline, carbon disulfide, and sulfur in an aniline method for making 2-mercaptobenzothiazole in presence of a catalyst,
    wherein the catalyst comprises a sulfonic acid type imidazolium ionic liquid.

2. The method as claimed in claim 1, wherein the sulfonic acid type imidazolium ionic liquid is [TSVM]HSO$_4$, [MPS]$_2$HSO$_4$, or a combination thereof;

structure of the [TSVM]HSO$_4$ is as follows:

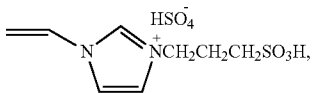

and structure of the [MPS]$_2$HSO$_4$ is as follows:

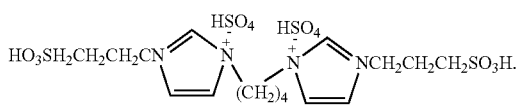

3. The method as claimed in claim 1, wherein the catalyst further comprises a carrier for supporting the sulfonic acid type imidazolium ionic liquid.

4. The method as claimed in claim 3, wherein the carrier is one or more selected from the group consisting of an activated alumina, a cordierite honeycomb ceramics, a mercaptoalkyl-functionalised silica gel, an ion exchange resin, and an HZSM molecular sieve.

5. The method as claimed in claim 4, wherein a weight ratio of the sulfonic acid type imidazolium ionic liquid and the carrier is (0.1 to 20):100.

6. The method as claimed in claim 4, wherein a reaction temperature is 200 to 280° C., reaction pressure is 3.0 to 8.0 MPa, and reaction time is 2 to 12 hours.

7. The method as claimed in claim 6, wherein the reaction temperature is 240 to 250° C., the reaction pressure is 4.5 to 5.5 MPa, and the reaction time is 4 to 6 hours.

8. The method as claimed in claim 1, wherein a molar ratio of the aniline, the carbon disulfide, and the sulfur is 1:(1.0 to 1.3):(1.1 to 2), and a weight ratio of the aniline and the sulfonic acid type imidazolium ionic liquid is 100:(1 to 5).

9. The method as claimed in claim 8, wherein the molar ratio of the aniline, the carbon disulfide, and the sulfur is 1:(1.0 to 1.1):(1.2 to 1.5), and the weight ratio of the aniline and the sulfonic acid type imidazolium ionic liquid is 100:(1 to 2).

10. The method as claimed in claim 1, wherein the 2-mercaptobenzothiazole is prepared by using a batchwise or a continuous production process.

11. The method as claimed in claim 2, wherein the catalyst further comprises a carrier for supporting the sulfonic acid type imidazolium ionic liquid.

12. The method as claimed in claim 11, wherein the carrier is one or more selected from the group consisting of an activated alumina, a cordierite honeycomb ceramics, a mercaptoalkyl-functionalised silica gel, an ion exchange resin, an HZSM molecular sieve, and a combination thereof.

13. The method as claimed in claim 12, wherein a weight ratio of the sulfonic acid type imidazolium ionic liquid and the carrier is (0.1 to 20):100.

14. The method as claimed in claim 5, wherein a reaction temperature is 200 to 280° C., reaction pressure is 3.0 to 8.0 MPa, and reaction time is 2 to 12 hours.

15. The method as claimed in claim 13, wherein a reaction temperature is 200 to 280° C., reaction pressure is 3.0 to 8.0 MPa, and reaction time is 2 to 12 hours.

16. The method as claimed in claim 14, wherein the reaction temperature is 240 to 250° C., the reaction pressure is 4.5 to 5.5 MPa, and the reaction time is 4 to 6 hours.

17. The method as claimed in claim 15, wherein the reaction temperature is 240 to 250° C., the reaction pressure is 4.5 to 5.5 MPa, and the reaction time is 4 to 6 hours.

* * * * *